United States Patent [19]

Friedrichs et al.

[11] Patent Number: 5,304,376

[45] Date of Patent: Apr. 19, 1994

[54] FUNGICIDAL COMPOSITION

[75] Inventors: Edmund Friedrichs, Ober-Hilbersheim; Guido Albert, Hackenheim, both of Fed. Rep. of Germany

[73] Assignee: Shell Internationale Research Maatschappij B.V., Netherlands

[21] Appl. No.: 468,895

[22] Filed: Jan. 23, 1990

[30] Foreign Application Priority Data

Feb. 3, 1989 [DE] Fed. Rep. of Germany ....... 3903247

[51] Int. Cl.$^5$ .................... A01N 25/08; A61K 9/16
[52] U.S. Cl. ..................... 424/409; 424/496; 424/497; 424/498
[58] Field of Search ............... 514/237.5; 424/78, 80, 424/81, 496, 497, 498

[56] References Cited

U.S. PATENT DOCUMENTS

| Re. 29,409 | 9/1977 | Yeager | 424/78 |
| 4,086,297 | 4/1978 | Rei et al. | 424/78 |
| 4,663,359 | 5/1987 | Rei | 521/85 |
| 4,753,934 | 6/1988 | Nickl et al. | 514/237.5 |
| 4,789,692 | 12/1988 | Rei et al. | 523/122 |
| 4,795,641 | 1/1989 | Kashdan | 424/438 |
| 4,910,200 | 3/1990 | Curtze et al. | 514/237.5 |

*Primary Examiner*—Thurman K. Page
*Assistant Examiner*—Peter F. Kulkosky

[57] ABSTRACT

A fungicidal composition in particulate or powder form wherein each active particle thereof comprises a fungicidally active compound, especially an acrylamide such as dimethomorph, dispersed in a polymer material having a melting point below the degradation temperature of the compound. The fungicidal composition is particularly useful in the form of a wettable powder or a suspension concentrate.

5 Claims, No Drawings

FUNGICIDAL COMPOSITION

The present invention relates to fungicidal compositions, a process for their preparation and their use in combating fungal infections, particularly in plants.

The present invention is concerned with the problem of formulating fungicides especially of the acrylamide type—see European Patent 120321—so that the inherent activity of the fungicide is maintained in an effective manner.

It is well known that fungal diseases in agricultural crops can be combated by the use of properly formulated active materials. Generally, these fungicidal formulations have to be applied early, before infection of the plant has taken place. Some diseases, however, are prompted by particular weather conditions—for instance heavy rainfalls, dry periods—and there is constant risk that an infection will occur earlier than expected. In unfavourable cases, an infection could have taken place before the fungicide was applied or before it was actually transported to its site of action. In that case, it is an undoubted advantage if an active material also acts after infection has taken place. Such an activity of a fungicide is called curative activity, in contrast to the ordinary performance which is called prophylactic activity.

A formulation has now been found which maintains the inherent activity of the fungicide and, in the case of acrylamide fungicides, enhances it in an effective manner so that the curative and prophylactic action occurs with consistency.

Accordingly the present invention provides a fungicidal composition in particulate or powder form wherein each active particle thereof comprises a fungicidally active compound dispersed in a polymer material having a melting point below the degradation temperature of the compound. For application, such a composition is normally formulated as a wettable powder or suspension concentrate and thus the invention also includes a fungicide composition which additionally includes at least one inert carrier, preferably at least two carriers one of which is a surface active agent.

The particle size of the fungicidal composition according to the invention will depend on the nature of the formulation. Generally speaking, the particle size will vary between 0.1 to 50 μm, preferably from 0.3 to 30 μm. In a wettable powder formulation a typical particle size range is 3 to 30 μm, preferably 5–15 μm whereas for a suspension concentrate the particle size range is 0.3 to 5 μm preferably 0.5 to 2.5 μm.

The polymer material can be a natural or synthetic macromolecular substance and is preferably a polyester, polyether, polyurethane, polyketone, polylactide, polylactic acid, polyacrylate, polycarbonate, polyamide, natural or synthetic rubber, natural or synthetic wax or resin, e.g. rosin or wood rosin, cellulose or cellulose derivative, homocellulose or lignin. More preferably, the polymer material is a polylactide, polylactic acid, polyacrylate, polyurethane, rosin or wood resin or a polyamide.

The fungicidally active compound may be any fungicide which can be incorporated into the polymer material without degradation during the incorporation process. Indeed, compositions according to the invention have been made from rosin with dodine, fenarimol, fenpropidin, fenpropinorph, imazalil sulphate, metalaxyl, penconazol, pyrifenox or triadimenol and from polyacrylate (PLEX 4968F) with fenpropidin or fenpropimorph. Preferably, such compositions have a ratio of polymer: active ingredient of 1:1. However, especially good results have been obtained with fungicidally active compounds of the general formula:

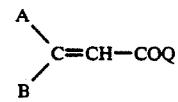

wherein
A represents

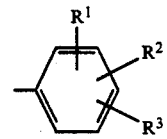

B represents

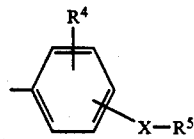

Q represents

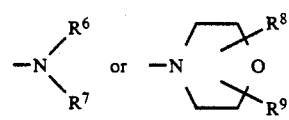

in which
$R^1$ is $C_{1-4}$-alkyl, $C_{1-4}$-alkoxy, $NH_2$, $NH(C_{1-4}$-alkyl), $N(C_{1-4}$-alkyl$)_2$, $C_{3-4}$ alkenyl, $C_{3-4}$ alkynyl, $C_{3-4}$ alkenyloxy, $C_{3-4}$ alkynyloxy or $C_{3-6}$ cycloalkyl;

$R^2$ is $C_{1-4}$-alkyl, $C_{1-4}$-alkoxy or halogen;

$R^3$ is hydrogen or halogen;

$R^4$ is hydrogen, halogen, $C_{1-4}$-alkyl or $C_{1-4}$-alkoxy;

$R^5$ is hydrogen, a phenyl group optionally substituted by one or more substituents selected from $C_{1-4}$-alkyl, $C_{1-4}$-alkoxy and halogen moieties, a $C_{1-12}$ alkyl group optionally substituted by one or more halogen atoms, a $C_3-C_7$-cycloalkyl, biphenyl or phenoxyphenyl group, a $C_{2-6}$-alkenyl or $C_{2-6}$-alkynyl group each optionally substituted by a phenyl group, or a naphthyl or $CC_{5-8}$-cycloalkenyl group;

—X is a single bond, —O—, $S(O)_p$—, —N=N—, —$CHR^9$—O—, —O—$CHR^9$—, $CHR^9$—$S(O_p)$—, —S-$(O_p)$—$CHR^9$—, —$C_nH_{2n}$— (with n=1–10), —HC=CH— or —C≡C—;

$R^6$ is $C_{1-4}$-alkyl, $C_{3-7}$-cycloalkyl, benzyl, $C_{3-4}$-alkenyl or $C_{3-4}$-alkynyl;

$R^7$ is $C_{1-4}$-alkyl;

$R^8$ is hydrogen, $C_{1-4}$-alkyl or $C_{1-4}$-alkoxy;

$R^9$ is hydrogen or $C_{1-4}$-alkyl; and p is 0, 1 or 2. The preferred compound has general formula I in which A is 3,4-dinethoxyphenyl, B is phenyl or 4-chlorophenyl, and Q is morpholinyl.

The concentration of the fungicidally active compound in the polymer material may vary widely; suitably it is in the range 10 to 90 4 by weight but is preferably in the range 25 to 75% by weight of the compound plus polymer material.

For ease of application, and as mentioned earlier, the fungicidal composition according to the invention may additionally comprise at least one inert carrier for the particulate or powder material, preferably at least two carriers one of which is a surface active agent.

The carrier may be a solid or liquid material, which may be inorganic or organic and of synthetic or natural origin. Typical solid carriers include natural and synthetic clays and silicates, for example natural silicas, for example diatomaceous earths, and aluminium silicates, for example kaolinites, montmorillonites and micas. Typical liquid carriers are ketones, for example methylnaphthalenones, and petroleum fractions, for example petroleum xylenes and light mineral oils. Also water may be a liquid carrier. Mixtures of liquids are often suitable.

One or more surface active agents and/or stickers can be included in the composition. The surface active agent may be a dispersing agent or a wetting agent; it may be non-ionic or ionic. Any of the surface-active agents usually applied in formulating pesticides may be used. Examples of surface-active agents are the sodium and calcium salts of polyacrylic acids and lignin and sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol, condensates of these with ethylene oxide and/or propylene oxide; condensation products of fatty alcohols or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as sodium dodecylbenzene sulphonate; and polymers of ethylene oxide and copolymers of ethylene oxide and propylene oxide.

The composition may be formulated as a wettable powder, microcapsules, a dust, granules, an emulsifiable concentrate, an emulsion or a suspension concentrate. Preferred formulations for a composition according to the present invention are a wettable powder or a suspension concentrate.

Wettable powders usually contain 25, 50 or 75% w of active ingredient and may contain in addition to inert solid material, 3-10% w of a dispersing agent and, when necessary, 0-10% w of a stabiliser, a penetrant and/or sticker. A suspension concentrate is a stable non-sedimenting, flowable product and usually contains 10-75% w active ingredient, 0.5-15% w of dispersing agent, 0.1-10% w of suspending agent, for example protective colloid and/or thixotropic agent, and 0-10% of other additives including, for example, a biocide, a defoamer, a corrosion inhibitor, a stabiliser, a penetrant and/or sticker, and as dispersant, water or an organic liquid in which the active ingredient is substantially insoluble; certain organic additives and/or inorganic salts may be dissolved in the dispersant to assist in preventing sedimentation or as anti-freeze for water.

In the formulated condition, the compositions may contain from 1.0% to 80% by weight of active ingredient, preferably in the range 20% to 60%. If another active ingredient is present then the preferred range is likely to be 5% to 40% by weight.

Especially good results in terms of curativity of fungal diseases have been obtained with compositions comprising at least one compound of general formula I wherein A represents 3,4-dimethoxyphenyl, B represents phenyl or 4-chlorophenyl and Q represents morpholinyl in a concentration ranging from 0.1% to 99% of the composition as fungicidal component. With this compound the best results could be achieved with a concentration of the fungicide in the range from 10% to 50% by weight of the composition and a polymer concentration ranging from 5% to 50% of the composition. As polymer any polymer material which has a melting temperature below the degradation temperature of the fungicide may be used. Good results have been obtained with polylactide, polylactic acid, polyacrylate, polyurethane, rosin (root resin wax) and polyamide.

The dispersion of the fungicidally active compound in the polymer material may be obtained by any of the known melting and/or blending procedures. However, it is advantageous to melt the fungicidal compound together with the selected polymer material, optionally in the presence of adjuvants and auxilliaries, and then to chill the melt below the melting temperature of the mixture. Subsequently, the quenched melt may be ground to produce a particulate or powder form of the melt according to known methods. The production of the formulation for use by the farmer can be carried out by methods known for the formulation of agrochemical compounds. This procedure is especially favourable to compounds of general formula I.

Accordingly the present invention further provides a process for the preparation of a fungicidal composition which comprises melting the fungicidally active compound together with the polymer material, cooling the mixture below its melting temperature, transforming the solidified melt into particulate or powder form and, optionally, mixing the particulate or powder material with at least one carrier or with at least two carriers one of which is a surface active agent to produce the desired formulation.

The compositions may be used for the treatment of any fungal disease of plants, especially of vines.

If desired the fungicidally active compound can be admixed with one or more different fungicidally active compounds to compliment the spectrum of activity of the first compound. This mixture of active ingredients can be incorporated into the same polymer particle and then formulated according to known techniques, or, alternatively, the mixture can be achieved by separately incorporating the different active ingredients into polymer particles and blending the different sets of polymer particles together.

The following examples further illustrate the compositions and their preparation according to the invention:

EXAMPLE 1

3-(3,4-Dimethoxyphenyl)-3-(4-chlorophenyl)acrylic acid morpholide (10 g) was mixed with finely powdered polylactide (10 g; Resomer 18 L, Boehringer Ingelheim, Ingelheim, F.R.G.) and then was heated in a beaker to 150° C. After 5 min a low viscous, neat melt was formed which was poured out onto a cold glass plate. It solidified well on cooling and was then broken into pieces. In order to prepare a wettable powder, the pieces were ground in a mortar to form a powder of the melt.

EXAMPLE 2

3-(3,4-Dimethoxyphenyl)-3-(4-chlorophenyl)acrylic acid morpholide (1kg) was mixed with finely powdered polylactide (1kg; Resomer 18 L, Boehringer Ingelheim, Ingelheim, F.R.G.) and the mixture passed through a double-screw extruder which had been heated up to 140°-170° C. The resulting melt was conducted onto a water-cooled, rotating drum where it cooled and solidified. Subsequently, the solidified material was broken into pieces and ground in a mill to form a powder of the solidified melt.

EXAMPLE 3

25% Wettable Powder formulation

| | |
|---|---|
| 25% | 3-(3,4-dimethoxyphenyl)-3-(4-chlorophenyl)-acrylic acid morpholide (common name: dimethomorph) |
| 25% | polyacetic acid (M.W. 1000–10000) |
| 2% | wetting agent (sodium alkylnaphthenesulfonate) |
| 8% | dispersing agent (calcium lignosulfonate) |
| 20% | silicic acid (carrier) |
| 20% | kaolin (carrier) |

Before formulation, the active ingredient was dispersed in the polymer and ground to a powder according to the method of Example 1.

EXAMPLE 4

25% Wettable Powder Formulation

| | |
|---|---|
| 25% | 3-(3,4-dimethoxyphenyl)-3-(4-chlorophenyl)-acrylic acid morpholide (common name: dimethomorph) |
| 25% | wood rosin wax (m.p. 70–120° C.) |
| 2% | wetting resin (sodium alkylnaphthenesulfonate) |
| 8% | dispersing agent (calcium lignosulfonate) |
| 20% | silicic acid (carrier) |
| 20% | kaolin (carrier) |

Before formulation, the active ingredient was dispersed in the polymer and ground to a powder according to the method of Example 1.

EXAMPLE 5

30% Wettable Powder Formulation

| | |
|---|---|
| 30% | 3-(3,4-dimethoxyphenyl)-3-phenylacrylic acid morpholide |
| 15% | polyurethane (m.p. 150–180° C.) |
| 2% | wetting agent (sodium alkylbenzenesulfonate) |
| 8% | dispersing agent (calcium lignosulfonate) |
| 25% | montmorillonite (carrier) |
| 20% | clay (carrier) |

Before formulation, the active ingredient was dispersed in the polymer material and ground to a powder according to the method of Example 1.

EXAMPLE 6

250g/l Suspension Concentrate Formulation

| | |
|---|---|
| 250 g/l | 3-(3,4-dimethoxyphenyl)-3-phenylacrylic acid morpholide |
| 150 g/l | polyamide wax (GS-Wachs HS 35, Georg Schütz, Bad Schwalbach, F.R.G.) |
| 50 g/l | dispersing agent (alkylnaphthalenesulfonic acid-formaldehyde copolymer) |
| 5 g/l | defoamer (dimethylpolysiloxane) |
| 5 g/l | biocide (Proxel GXL, ICI) |
| 30 g/l | thickener (Shellflo S, Shell Int. Chem. Comp) |
| 80 g/l | antifreeze (propylene glycol) |
| up to 1000 ml | demineralised water |

Before formulation, the active ingredient was dispersed in the polymer and ground to a powder according to the method of Example 2.

COMPARATIVE EXAMPLE

50% wettable powder

| | |
|---|---|
| 50% | 3-(3,4-dimethoxyphenyl)-3-(4-chlorophenyl)-acrylic acid morpholide (common name: dimethomorph) |
| 2% | wetting agent (sodium alkylnaphthenesulfonate) |
| 8% | dispersing agent (calcium lignosulfonate) |
| 20% | silicic acid (carrier) |
| 20% | kaolin (carrier) |

Biological Testing Curative Activity of Fungicidal Composition against Plasmopara viticola Test plants:

Cuttings of the vine cultivar Müller-Thurgau were grown in the greenhouse at 25° C. and 50%–70% relative humidity. Plants were cultivated in plastic pots (diam. 12 cm). When 6–8 leaves had developed the plants were cut back to 3–4 equally sized leaves.

Infection:

The plants were artificially infected with an aqueous spore suspension of Plasmopara viticola containing 200,000 spores/ml. Infection was accomplished by spraying the lower side of leaves with the spore suspension. Then the plants were immediately incubated at 100% relative humidity for 48 hours.

Application:

4–6 plants per treatment were used. Application of the fungicidal compositions was carried out 48 hours after infection. The test plants were sprayed to run off in a spray cabinet using 20 ml of spray wash.

Then the plants were kept at high humidity in the greenhouse at 23° C. day and 18° C. night temperature until symptoms developed (approx. 5–6 days after infection).

Evaluation:

Evaluation was carried out by estimating the percentage of diseased leaf area of each individual leaf. The activity in % was calculated using the formula:

$$\% \text{ activity} = 100 - \frac{\% \text{ infected in treated}}{\% \text{ infection in untreated}} \times 100$$

Results:

Curative activity of several formulations against Plasmopara viticola in vines (concentration active ingredient: 150 ppm).

|  |  | Activity |
|---|---|---|
| Example 3, | WP 25 | 50% |
| Example 4, | WP 25 | 60% |
| Comp. example, | WP 50 | <10% |

These results illustrate the superior curative activity of the fungicidal compositions according to the invention over the known formulation.

We claim:

1. A method for the treatment of a fungal disease on a plant, comprising the steps of applying to said plant a fungicidally effective amount of a composition in particulate or powder form wherein each particle thereof comprises the active ingredient 3-(3,4-dimethoxyphenyl)-3-(4-chlorophenyl)-acrylic acid morpholide dispersed in a polymer material having a melting point below the degradation temperature of said active ingredient, said polymer material being selected from the group consisting of polyester, polyether, polyurethane, polyketone, polylactide, polylactic acid, polyacrylate, polycarbonate, polyamide, natural or synthetic rubber, natural or synthetic wax or resin, cellulose or cellulose derivative, homocellulose or lignin.

2. The method of claim 1 wherein said composition is prepared by the steps of combining said active ingredient with said polymer material in a melt state, cooling the thus-formed admixture to below the melting temperature of said polymer, and forming particulate or powder material from said admixture.

3. The method of claim 1 wherein said polymer material is polyactic acid.

4. The method of claim 1 wherein said polymer material is wood rosin wax.

5. The method of claim 1 wherein said composition comprises from about 10 to 90% by weight of said active ingredient.

* * * * *